(12) United States Patent
Weichert et al.

(10) Patent No.: US 6,617,344 B2
(45) Date of Patent: Sep. 9, 2003

(54) HETEROCYCLICALLY SUBSTITUTED BENZOYLGUANIDINES, PROCESS FOR THEIR PREPARATION, THEIR USE AS MEDICAMENTS OR DIAGNOSTICS, AND MEDICAMENTS COMPRISING THEM

(75) Inventors: Andreas Weichert, Egelsbach (DE); Udo Albus, Florstadt (DE); Hans-Willi Jansen, Niedemhausen (DE); Heinz-Werner Kleemann, Bischofsheim (DE); Hans-Jochen Lang, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/352,216

(22) Filed: Jan. 28, 2003

(65) Prior Publication Data

US 2003/0139607 A1 Jul. 24, 2003

Related U.S. Application Data

(63) Continuation of application No. 10/075,394, filed on Feb. 15, 2002, now abandoned, which is a continuation of application No. 09/901,624, filed on Jul. 11, 2001, now abandoned, which is a continuation of application No. 09/692,317, filed on Oct. 20, 2000, now abandoned.

(30) Foreign Application Priority Data

Oct. 22, 1999 (DE) ............................ 199 50 898

(51) Int. Cl.⁷ .................. A61K 31/4184; C07D 235/16
(52) U.S. Cl. .................. 514/394; 514/399; 548/309.7; 548/336.5
(58) Field of Search .................. 548/336.5, 309.7; 514/394, 399

(56) References Cited

U.S. PATENT DOCUMENTS 5,665,739 A 9/1997 Lang et al.
5,753,680 A 5/1998 Gericke et al.
5,965,744 A 10/1999 Weichert et al.

FOREIGN PATENT DOCUMENTS

EP 0 602 523 A1 6/1994
EP 0 640 588 A1 3/1995

OTHER PUBLICATIONS

Manfred Baumgarth et al., (2–Methyl–5–(methylsulfonyl)benzoyl)guanidine $Na^+/H^+$ Antiporter Inhibitors, 1997, J. Med. Chem., vol. 40, pp. 2017–2034.

Primary Examiner—Laura L. Stockton
(74) Attorney, Agent, or Firm—Finnegan, Henderson, Farabow, Garrett & Dunner, LLP

(57) ABSTRACT

Heterocyclically substituted benzoylguanidines of the formula I

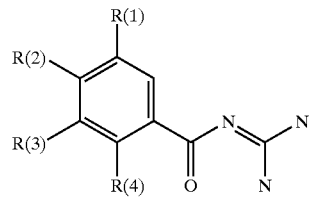

in which the substituents R(1) to R(4) have the meanings indicated in the claims.

These compounds I are suitable as antiarrhythmic pharmaceuticals having a cardioprotective component for infarct prophylaxis and infarct treatment, and also for the treatment of angina pectoris.

They also preventively inhibit the pathophysiological processes in the formation of ischemically induced damage, in particular in the elicitation of ischemically induced cardiac arrhythmias.

15 Claims, No Drawings

HETEROCYCLICALLY SUBSTITUTED BENZOYLGUANIDINES, PROCESS FOR THEIR PREPARATION, THEIR USE AS MEDICAMENTS OR DIAGNOSTICS, AND MEDICAMENTS COMPRISING THEM

This application is a continuation of application Ser. No. 10/075,394, filed Feb. 15, 2002 (the contents of which are incorporated by reference herein), now abandoned, which is a continuation of application Ser. No. 09/901,624, filed Jul. 11, 2001 now abandoned, which is a continuation of application Ser. No. 09/692,317, filed Oct. 20, 2000 now abandoned.

This application claims the benefit of foreign priority under 35 USC §119 to German patent application no. 19950898.4, filed on Oct. 22, 1999, the contents of which are incorporated by reference herein.

The invention relates to heterocyclically substituted benzoylguanidines of the formula I

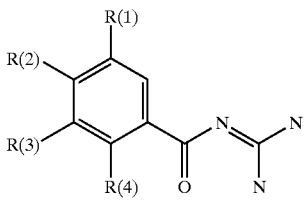

in which:
R(1) is —(CF$_2$)$_c$—CF$_3$;
c is zero, 1, 2 or 3;
R(2) is (C$_1$–C$_9$)-heteroaryl, linked via C or N, which is unsubstituted or substituted by 1–3 substituents selected from the group consisting of F, Cl, CF$_3$, CH$_3$, methoxy, hydroxyl, amino, methylamino and dimethylamino;
R(3) is H, F, Cl, Br, I, CN, NO$_2$ or (C$_1$–C$_8$)-alkyl;
R(4) is H, (C$_1$–C$_4$)-alkyl, (C$_1$–C$_4$)-alkoxy, F, Cl, Br, I, CN or —(CF$_2$)$_o$—CF$_3$;
o is zero, 1 or 2;
and their pharmaceutically tolerable salts.

Preferred compounds of the formula I are those in which:
R(1) is trifluoromethyl;
R(2) is imidazolyl or benzimidazolyl, linked via C or N, each of which is unsubstituted or substituted by 1–3 substituents selected from the group consisting of F, Cl, CF$_3$, CH$_3$, methoxy, hydroxyl, amino, methylamino and dimethylamino;
R(3) is H, F, Cl or (C$_1$–C$_4$)-alkyl;
R(4) is H, (C$_1$–C$_4$)-alkyl, (C1–C$_4$)-alkoxy, F, Cl or CF$_3$;
and their pharmaceutically tolerable salts.

Very particularly preferred compounds of the formula I are those in which:
R(1) is trifluoromethyl;
R(2) is imidazolyl or benzimidazolyl, linked via N, each of which is unsubstituted or substituted by 1–3 substituents selected from the group consisting of F, Cl, CF$_3$, CH$_3$ and methoxy;
R(3) is H;
R(4) is H, methyl, methoxy, Cl or CF$_3$;
and their pharmaceutically tolerable salts.

(C$_1$–C$_9$)-heteroaryl is understood as meaning radicals which are derived from phenyl or naphthyl, in which one or more CH groups are replaced by N and/or in which at least two adjacent CH groups-are replaced by S, NH or O (with formation of a five-membered aromatic ring). In addition, one or both atoms of the condensation site of bicyclic radicals (such as in indolizinyl) can also be nitrogen atoms.

(C$_1$–C$_9$)-heteroaryl is in particular furanyl, thienyl, pyrrolyl, imidazolyl, benzimidazole, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl; very particularly imidazolyl or benzimidazolyl.

If one of the substituents R(1) to R(4) contains one or more asymmetric centers, these can be either of the S or R configuration. The compounds can be present as optical isomers, as diastereomers, as racemates or as mixtures thereof.

The designated alkyl radicals can be either straight-chain or branched.

The invention furthermore relates to a process for the preparation of the compound 1, which comprises reacting compounds of the formula II

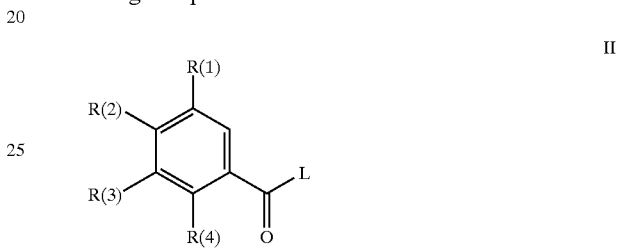

in which R(1) to R(4) have the meaning indicated and L is an easily nucleophilically substitutable leaving group, with guanidine.

The activated acid derivatives of the formula II, in which L is an alkoxy group, preferably a methoxy group, a phenoxy group, a phenylthio, methylthio or 2-pyridylthio group, a nitrogen heterocycle, preferably 1-imidazolyl, are advantageously obtained in a manner known per se from the underlying carbonyl chlorides (formula II, L=Cl), which in turn can be prepared in a manner known per se from the underlying carboxylic acids (formula II, L=OH), for example using thionyl chloride. In addition to the carbonyl chlorides of the formula II (L=Cl), further activated acid derivatives of the formula II can also be prepared directly from the underlying benzoic acid derivatives (formula II, L=OH) in a manner known per se, such as, for example, the methyl esters of the formula II where L=OCH$_3$ by treating with gaseous HCl in methanol, the imidazolides of the formula II by treating with carbonyidiimidazole [L=1-imidazolyl, Staab, Angew. Chem. Int. Ed. Engl. 1, 351–367 (1962)], the mixed anhydrides II using Cl—COOC$_2$H$_5$ or tosyl chloride in the presence of triethylamine in an inert solvent, and also the activation of benzoic acids using dicyclohexylcarbodiimide (DCC) or using O-[(cyano(ethoxycarbonyl)methylene)amino]-1,1,3,3-tetramethyluronium tetrafluoroborate ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are indicated stating source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. Methanol, isopropanol and THF from 20° C. up to the boiling temperature of these solvents have proven suitable here in the reaction of the methyl benzoates (II, L=OMe) with guanidine. Most reactions of compounds II with salt-free guanidine were advantageously carried out in aprotic inert solvents such as THF, dimethoxyethane and dioxane. However, using a base such as, for example, NaOH, water can also be used as a solvent in the reaction of II with guanidine.

If L=Cl, the reaction is advantageously carried out with addition of an acid scavenger, e.g. in the form of excess guanidine for removing the hydrohalic acid.

Some of the underlying benzoic acid derivatives of the formula II are known and described in the literature. The unknown compounds of the formula II can be prepared by methods known from the literature. The benzoic acids obtained are reacted to give compounds I according to the invention according to one of the process variants described above.

The introduction of some substituents into the 2, 3, 4 and 5 positions is possible by methods, known from the literature, of palladium-mediated cross-coupling of aryl halides or aryl triflates with, for example, organostannanes, organoboronic acids or organoboranes or organocopper or -zinc compounds.

In general, benzoylguanidines I are weak bases and can bind acid with formation of salts. Possible acid addition salts are salts of all pharmacologically. tolerable acids, for example halides, in particular hydrochlorides, lactates, sulfates, citrates, tartrates, acetates, phosphates, methylsulfonates, p-toluenesulfonates.

European Patents EP 602 523 (HOE 92/F 405) and EP 640 588 (HOE 93/F 254) describe benzoylguanidines of similar constitution, which also carry fluorinated alkyl substituents in the 5 position in addition to a multiplicity of other substituents R(1), and can also carry ($C_1$–$C_9$) heteroaryls in the 4 position in addition to a multiplicity of substituents.

However, it was not to be foreseen that these compounds having fluoroalkyl and hetaryl substitution especially would display an outstanding action.

Surprisingly, the compounds according to the invention are NHE inhibitors which additionally inhibit the noninactivating sodium channel (veratridine-activatable sodium channel) induced during ischemia, to which the outstanding action can be attributed. As a result of their pharmacological properties, the compounds are outstandingly suitable as antiarrhythmic pharmaceuticals having a cardioprotective component for infarct prophylaxis and infarct treatment, and also for the treatment of angina pectoris, where they also preventively inhibit or greatly decrease the pathophysiological processes in the formation of ischemically induced damage, in particular in the elicitation of ischemically induced cardiac arrhythmias. Because of their protective actions against pathological hypoxic and ischemic situations, the compounds of the formula I according to the invention can be used, as a result of inhibition of the cellular $Na^+/H^+$ exchange mechanism, as pharmaceuticals for the treatment of all acute or chronic damage caused by ischemia or illnesses induced primarily or secondarily thereby. This relates to their use as pharmaceuticals for surgical interventions, e.g. in organ transplantations, where the compounds can be used for the protection of organs in the donor before and during removal, for the protection of removed organs, for example during treatment with or storage thereof in physiological bathing fluids, and also during transfer to the recipient's body. The compounds are also valuable pharmaceuticals having a protective action when carrying out angioplastic surgical interventions, for example on the heart and also on peripheral vessels. Corresponding to their protective action against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula I according to the invention are also suitable for the treatment of forms of shock, such as, for example, of allergic, cardiogenic, hypovolemic and of bacterial shock.

Moreover, the compounds of the formula I according to the invention are distinguished by strong inhibitory action on the proliferation of cells, for example fibroblast cell proliferation and the proliferation of smooth vascular muscle cells. The compounds of the formula I are therefore suitable as valuable therapeutics for illnesses in which cell proliferation is a primary or secondary cause, and can therefore be used as antiatherosclerotics, agents against diabetic late complications, carcinomatous diseases, fibrotic diseases such as pulmonary fibrosis, hepatic fibrosis or renal fibrosis, organ hypertrophy and hyperplasia, in particular in prostate hyperplasia or prostate hypertrophy.

The compounds according to the invention are efficacious inhibitors of the cellular sodium/proton antiporter ($Na^+/H^+$ exchanger), which is raised in numerous diseases (essential hypertension, atherosclerosis, diabetes etc.) even in those cells which are easily accessible to measurements, such as, for example, in erythrocytes, platelets or leukocytes. The compounds according to the invention are therefore suitable as excellent and simple scientific tools, for example in their use as diagnostics for the determination and differentiation of certain forms of hypertension, but also of atherosclerosis, of diabetes, proliferative diseases etc. Moreover, the compounds of the formula I are suitable for preventive therapy for the prevention of the genesis of high blood pressure, for example of essential hypertension.

Pharmaceuticals which contain a compound I can in this case be administered orally, parenterally, intravenously, rectally or by inhalation, the preferred administration being dependent on the particular course of the disease. The compounds I can be used here on their own or together with pharmaceutical excipients, namely both in veterinary and in human medicine.

The person skilled in the art is familiar on the basis of his/her expert knowledge with excipients which are suitable for the desired pharmaceutical formulation. In addition to solvents, gel-forming agents, suppository bases, tablet excipients and other active compound carriers, it is possible to use, for example, antioxidants, dispersants, emulsifiers, antifoams, flavor corrigents, preservatives, solubilizers or colorants.

For an oral administration form, the active compounds are mixed with the additives suitable for this, such as vehicles, stabilizers or inert diluents, and brought by means of the customary methods into the suitable administration forms, such as tablets, coated tablets, hard gelatin capsules, aqueous, alcoholic or oily solutions. Inert carriers which can be used are, for example, gum arabic, magnesia, magnesium carbonate, potassium phosphate, lactose, glucose or starch, in particular corn starch. In this case, preparation can be carried out both as dry and as moist granules. Possible oily vehicles or solvents are, for example, vegetable or animal oils, such as sunflower oil or cod-liver oil.

For subcutaneous or intravenous administration, the active compounds, if desired with the substances customary for this such as solubilizers, emulsifiers or further excipients, are brought into solution, suspension or emulsion. Suitable solvents are, for example, water, physiological saline solution or alcohols, e.g. ethanol, propanol, glycerol, in addition also sugar solutions such as glucose or mannitol solutions, or otherwise a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If desired, the formulation can also contain still other pharmaceutical excipients such as surfactants, emulsifiers and stabilizers and also a propellant. Such a preparation customarily contains the active compound in a concentration of approximately 0.1 to 10, in particular from approximately 0.3 to 3, % by weight.

The dose of the active compound of the formula I to be administered and the frequency of administration depend on the potency and duration of action of the compounds used; additionally also on the type and severity of the illness to be treated and on the sex, age, weight and individual responsiveness to be treated.

On average, the daily dose of a compound of the formula I in the case of a patient weighing approximately 75 kg is at least 0.001 mg/kg, preferably 0.01 mg/kg, at most 10 mg/kg, preferably 1 mg/kg, of body weight. In the case of acute episodes of the illness, for example immediately after suffering a cardiac infarct, even higher and especially more frequent doses may also be necessary, e.g. up to 4 individual doses per day. In particular in the case of i.v. administration, for example in the case of an infarct patient in the intensive care unit, up to 200 mg per day may be necessary.

EXPERIMENTAL SECTION

General Procedure for the Preparation of Benzoylguanidines (I)

Variant A: From Benzoic Acids (II, L=OH)

1.0 eq of the benzoic acid derivative of the formula II is dissolved or suspended in anhydrous THF (5 ml/mmol) and then treated with 1.1 eq of carbonyidiimidazole. After stirring for 2 hours at RT, 5.0 eq of guanidine are introduced into the reaction solution. After stirring overnight, the THF is distilled off under reduced pressure (Rotavapor), the residue is treated with water, the mixture is adjusted to pH 6 to 7 using 2N HCl and the corresponding benzoylguanidine (formula 1) is filtered off. The benzoyl-guandines thus obtained can be converted into the corresponding salts by treating with aqueous, methanolic or ethereal hydrochloric acid or other pharmacologically tolerable acids.

General Procedure for the Preparation of Benzoylguanidines (I)

Variant B: From Alkyl Benzoates (II, L=O-alkyl)

1.0 eq of the alkyl benzoate of the formula II and 5.0 eq of guanidine (free base) are dissolved in isopropanol or suspended in THF and heated to reflux (typical reaction time 2 to 5 h) until conversion is complete (thin-layer checking). The solvent is distilled off under reduced pressure (Rotavapor), the residue is taken up in EA and the mixture is washed 3× with NaHCO$_3$ solution. It is dried over Na$_2$SO$_4$, the solvent is distilled off in vacuo and the residue is chromatographed on silica gel using a suitable eluent, e.g. EA/MeOH 5:1.

(For salt formation compare variant A)

EXPERIMENTAL SECTION

| Abbreviations: | |
|---|---|
| DCl | direct chemical ionization |
| DMF | N,N-dimethylformamide |
| ES+ | electrospray ionization |
| eq | equivalents |
| EtOH | ethanol |
| h | hour |
| HCl | hydrogen chloride |
| LM | solvent |
| MeOH | methanol |
| NaOH | sodium hydroxide solution |
| RF | reflux |

| -continued | |
|---|---|
| Abbreviations: | |
| RT | room temperature |
| m.p. | melting point |
| THF | tetrahydrofuran |
| TMEDA | tetramethylethylenediamine |

Example 1

4-N-Imidazolyl-3-trifluoromethylbenzoylguanidine Dihydrochloride

Colorless crystals, m.p. 244–248° C.

Synthesis Route:

a) 4-N-Imidazolyl-3-trifluoromethylbenzoylguanidine from 4-fluoro-3-trifluoromethylbenzoic acid by activation with 1.2 eq of carbonyldiimidazole in THF at 50° C. After stirring for 1.5 h, 3 eq of guanidine and 2 eq of imidazole are added, then the mixture is stirred at 120° C. in DMF for a further 7 h and then subjected to aqueous work-up. The product precipitates as a solid and is filtered off with suction, m.p. 245–250° C., M$^+$+H=298 (DCl).

b) 4-N-Imidazolyl-3-trifluoromethylbenzoylguanidine dihydrochloride from 1 a) using 0.5 N EtOH/HCl at RT; the solid is filtered off with suction.

Example 2

4-N-(4'-Methylimidazolyl)-3-trifluoromethylbenzoylguanidine Dihydrochloride

Colorless crystals, m.p. 236° C.

Synthesis Route:

a) 4-Fluoro-3-trifluoromethylbenzoylguanidine from methyl 4-fluoro-3-trifluoromethylbenzoate by guanidation using 3 eq of guanidine in THF for 2 h at RF, followed by aqueous work-up and suction filtration of the solid, m.p. 165° C., M$^+$+H=250 (ES$^+$).

b) 4-N-(4'-Methylimidazolyl)-3-trifluoromethylbenzoylguanidine from 2 a) by nucleophilic replacement of the fluorine atom using 2 eq of 4-methylimidazole in the presence of 6 eq of potassium carbonate in DMF with heating to 100° C. for 10 h. After aqueous work-up, purification by column chromatography follows, M$^+$+H=312 (ES$^+$).

c) 4-N-(4'-Methylimidazolyl)-3-trifluoromethylbenzoylguanidine dihydrochloride from 2 b) using ether/HCl at RT; the solid is filtered off with suction.

Example 3

4-N-(4',5'-Dimethylimidazolyl)-3-trifluoromethylbenzoyl-guanidine Dihydrochloride:

Colorless Crystals, m.p. 259–262° C., M$^+$+H=326 (ES$^+$)

Synthesis Route:

a) 4-N-(4',5'-Dimethylimidazolyl)-3-trifluoromethylbenzoylguanidine from 2 a) by nucleophilic replacement analogously to 2 b), using 4,5-dimethylimidazole. After aqueous work-up, the solid is filtered off with suction, m.p. 264° C. (dec.), M$^+$+H=326 (ES$^+$).

b) 4-N-(4',5'-Dimethylimidazolyl)-3-trifluoromethylbenzoylguanidine dihydrochloride from 3 a) by hydrochloride formation analogously to 2 c).

Example 4

4-N-Benzimidazolyl-3-trifluoromethylbenzoylguanidine Dihydrochloride

Colorless crystals, m.p. 183° C., M$^+$+H=348 (ES$^+$).
Synthesis Route:
a) 4-N-Benzimidazolyl-3-trifluoromethylbenzoylguanidine from 2 a) analogously to 3 a), using benzimidazole. After aqueous work-up, purification by column chromatography on silica gel using dichloromethane/methanol (20:1) follows.
b) 4-N-Benzimidazolyl-3-trifluoromethylbenzoylguanidine dihydrochloride from 4 a) analogously to 2 c).

Example 5

4-N-(5',6'-Dichlorobenzimidazolyl)-3-trifluoromethylbenzoylguanidine Dihydrochloride:
Colorless Crystals, m.p. 226–227° C.
Synthesis Route:
a) Methyl 4-fluoro-3-trifluoromethylbenzoate from 4-fluoro-3-trifluoromethylbenzoic acid using 1.1 eq of carbonylbisimidazole in THF and with stirring for 2 h at RT and subsequent addition of an excess of methanol. After a further 2 h at RT, an aqueous work-up follows; extraction with ethyl acetate yields a yellowish oil, M$^+$+H=223 (DCI).
b) 4-N-(5',6'-Dichlorobenzimidazolyl)-3-trifluoromethylbenzoic acid from 5 a) analogously to 2b), using 2 eq of 5,6-dichlorobenzimidazole, M$^+$+H=375 (ES$^+$).
c) 4-N-(5',6'-Dichlorobenzimidazolyl)-3-trifluoromethylbenzoylguanidine from 5 b) by activation with 1 eq of carbonylbisimidazole at RT for 2 h in DMF, and subsequent addition of 5 eq of guanidine hydrochloride and 7 eq of N-ethyldiisopropylamine. After stirring at RT for 1 h, an aqueous work-up follows, the solid is filtered off with suction, M$^+$+H=416 (FAB).
d) 4-N-(5',6'-Dichlorobenzimidazolyl)-3-trifluoromethylbenzoylguanidine dihydrochloride from 5 c) analogously to 2 c).

Example 6

4-N-(5',6'-Dimethylbenzimidazolyl)-3-trifluoromethylbenzoylguanidine Dihydrochloride:
Colorless Crystals, m.p. 255° C.
Synthesis Route:
a) 4-N-(5',6'-Dimethylbenzimidazolyl)-3-trifluoromethylbenzoic acid from 5 a) by nucleophilic replacement with 2 eq of 5,6-dimethylbenzimidazole in the presence of 3.7 eq of potassium carbonate in DMF in the course of 2 h at 120° C. Aqueous work-up, extraction with ether yields an oil, M$^+$+H=335 (ES$^+$).
b) 4-N-(5',6'-Dimethylbenzimidazolyl)-3-trifluoromethylbenzoylguanidine from 6 a) by guanidation analogously to 2 a) affords a solid after aqueous work-up, m.p. 233° C.
c) 4-N-(5',6'-Dimethylbenzimidazolyl)-3-trifluoromethylbenzoylguanidine dihydrochloride from 5 b) analogously to 2 c).

Example 7

4-N-(4',5'-Dimethylimidazolyl)-2-methyl-5-trifluoromethylbenzoylguanidine Dihydrochloride:
Colorless Crystals, m.p. 235° C.
Synthesis Route
a) Methyl 4-fluoro-2-methyl-5-trifluoromethylbenzoate by lithiation of 4-fluoro-3-trifluoromethylbenzoic acid with 3 eq of s-butyllithium in the presence of 2.95 eq of TMEDA at −90° C. under argon in THF and subsequent reaction with 3 eq of methyl iodide. The mixture is warmed to RT in the course of 1.5 h and subjected to aqueous work-up. Extraction with ethyl acetate yields an oil, which is distilled in a bulb tube in a high vacuum and obtained as a yellowish oil, M$^+$+H=237(DCI).
b) 4-Fluoro-2-methyl-5-trifluoromethylbenzoic acid from 7 a) by hydrolysis with 2N NaOH in MeOH at RT overnight, followed by aqueous work-up and extraction with ethyl acetate, M$^+$+H=223 (DCI).
c) 4-Fluoro-2-methyl-5-trifluoromethylbenzoylguanidine from 7 b) by reaction with 1.1 eq of thionyl chloride in toluene with heating to RF for 1 h. The solvent is then evaporated and the intermediate acid chloride is reacted at RT in THF with a solution of 3 eq of guanidine hydrochloride and 5 eq of 2N NaOH in THF. After aqueous work-up, the solid is filtered off with suction, m.p. 175–177° C., M$^+$+H=264 (DCI).
d) 4-N-(4',5'-Dimethylimidazolyl)-2-methyl-5-trifluoromethylbenzoylguanidine from 7 c) by nucleophilic replacement with 2 eq of 4,5-dimethylimidazole in the presence of 4 eq of potassium carbonate at 120° C. in DMF in the course of 12 h. Aqueous work-up, extraction with ethyl acetate and subsequent purification by column chromatography (silica gel) using dichloromethane/methanol (20:1) yields a solid, m.p. 245° C., M$^+$+H=390 (ES$^+$).
e) 4-N-(4',5'-Dimethylimidazolyl)-2-methyl-5-trifluoromethylbenzoylguanidine dihydrochloride from 7 d) analogously to 2 c).

Example 8

4-N-Benzimidazolyl-2-methyl-5-trifluoromethylbenzoylguanidine Dihydrochloride colorless crystal, m.p. 199–202° C.
Synthesis Route:
a) 4-N-Benzimidazolyl-2-methyl-5-trifluoromethylbenzoic acid from 7 a) by nucleophilic replacement of the fluorine with benzimidazole analogously to 7 d) and subsequent hydrolysis using NaOH. Aqueous work-up yields a solid, M$^+$+H=321 (ES$^+$).
b) 4-N-Benzimidazolyl-2-methyl-5-trifluoromethylbenzoylguanidine from 8 a) by guanidation analogously to 5 c), M$^+$+H=362 (ES$^+$).
c) 4-N-Benzimidazolyl-2-methyl-5-trifluoromethylbenzoylguanidine dihydrochloride from 8 b) by hydrochloride formation analogously to 2 c).

Example 9

2-Chloro-4-N-benzimidazolyl-3-trifluoromethylbenzoylguanidine Dihydrochloride:
Colorless Crystals, m.p. 193–196° C., M$^+$+H=382 (ES$^+$).
Synthesis Route:
a) 2-Chloro4-fluoro-5-iodobenzoic acid from 2-chloro-4-fluorobenzoic acid by iodination with 1.2 eq of N-iodosuccinimide in 12 eq of trifluoromethanesulfonic acid at 0° C. for 2 h. The reaction mixture is added to ice/H$_2$O and the solid is filtered off with suction, m.p. 160–168° C., M$^+$+H=300 (DCI).
b) Methyl 2-chloro-4-fluoro-5-iodobenzoate from 9a) by esterification in MeOH/HCl at RT for 20 h, aqueous work-up and extraction with ethyl acetate affords a yellow oil, M$^+$+H=315 (DCI).
c) Methyl 2-chloro4-fluoro-5-trifluoromethylbenzoate from 9 b) by trifluoromethylation with 2 eq of trifluoroacetic acid potassium salt and 2.05 eq of copper(I) iodide in DMF for 4 h at 150° C. Aqueous work-up, extraction with ethyl acetate and subsequent column chromatography on silica gel using n-heptane/ethyl acetate (9:1) yields a brownish liquid, M⁺+H=257 (DCl).

d) Methyl 2-chloro4-N-benzimidazolyl-5-trifluoromethylbenzoate from 9c) by reaction with 1.1 eq of benzimidazole and 3.2 eq of potassium carbonate at RT in DMF in the course of 1.5 h. Aqueous work-up and extraction with ethyl acetate yields an oil, M⁺+H=355 (FAB).

e) 2-Chloro-4-N-benzimidazolyl-5-trifluoromethylbenzoic acid from 9 d) by hydrolysis with 2N NaOH in methanol at RT for 18 h. Aqueous work-up yields a solid, M⁺=341 (ES⁺).

f) 2-Chloro-4-N-benzimidazolyl-5-trifluoromethylbenzoylguanidine from 9 e) by reaction with 2.3 eq of carbonylbisimidazole for 2 h at RT in THF, subsequent addition of 4 eq of guanidine and stirring for a further 3 h at RT yields, after aqueous work-up, a solid, M⁺+H=382(ES⁺).

g) Hydrochloride formation from 9 f) analogously to 2 c).

Example 10

2-Chloro-4-N-(5',6'-dichlorobenzimidazolyl)-5-trifluoromethylbenzoylguanidine Dihydrochloride: Colorless Crystals, m.p. 199–200° C.

Synthesis Route:

a) Methyl 2-chloro4-N-(5',6'-dichlorobenzimidazolyl)-5-trifluoromethylbenzoate from 9 c) analogously to 10 a), but using 5,6-dichlorobenzimidazole, colorless oil, M⁺+H=423 (FAB).

b) 2-Chloro-4-N-(5',6'-dichlorobenzimidazolyl)-5-trifluoromethylbenzoic acid from 10 a) analogously to 9 e), colorless solid, M⁺+H=409 (ES⁺).

c) 2-Chloro-4-N-(5',6'-dichlorobenzimidazolyl)-5-trifluoromethyl-benzoylguanidine from 10 b) analogously to 9 f), colorless solid, M⁺+H=450 (ES⁺).

d) 2-Chloro4-N-(5',6'-dichlorobenzimidazolyl)-5-trifluoromethylbenzoylguanidine dihydrochloride from 10 c) analogously to 2 c).

We claim:

1. A heterocyclically substituted benzoylguanidine of formula I

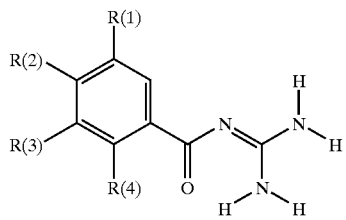

in which:
R(1) is —(CF₂)c—CF₃;
c is zero, 1, 2 or 3;
R(2) is benzimidazolyl, linked via C or N, which is unsubstituted or substituted by 1–3 substituents selected from the group consisting of F, Cl, CF₃, CH₃, methoxy, hydroxyl, amino, methylamino and dimethylamino;
R(3) is H, F, Cl, Br, I, CN, NO₂ or (C₁–C₈)-alkyl;
R(4) is (C₁–C₄)-alkyl, (C₁–C₄)-alkoxy, F, Cl, Br, I, CN or —(CF₂)ₒ—CF₃;
o is zero, 1 or 2;
or a pharmaceutically tolerable salt thereof.

2. A compound of claim 1, wherein:
R(1) is trifluoromethyl;
R(3) is H, F, Cl or (C₁–C₄)-alkyl;
R(4) is (C₁–C₄)-alkyl, (C₁–C₄)-alkoxy, F, Cl or CF₃.

3. A compound of claim 1, wherein:
R(1) is trifluoromethyl;
R(2) is benzimidazolyl, linked via N, which is unsubstituted or substituted by 1–3 substituents selected from the group consisting of F, Cl, CF₃, CH₃ and methoxy;
R(3) is H;
R(4) is methyl, methoxy, Cl or CF₃.

4. A process for preparing a compound of formula I of claim 1, which comprises reacting a compound of formula II

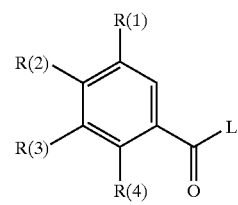

in which R(1) to R(4) have the meaning indicated and L is an easily nucleophilically substitutable leaving group, with guanidine.

5. A method of treating or preventing an illness caused by an ischemic condition, comprising administering an effective amount of a compound of claim 1 to a host in need of such treatment or prevention.

6. A method of treating or preventing cardiac infarct, comprising administering an effective amount of a compound of claim 1 to a host in need of such treatment or prevention.

7. A method of treating or preventing angina pectoris, comprising administering an effective amount of a compound of claim 1 to a host in need of such treatment or prevention.

8. A method for the treatment or prevention of an ischemic condition of the heart, comprising administering an effective amount of a compound of claim 1 to a host in need of each treatment or prevention.

9. A method for the treatment or prevention of stroke or of an ischemic condition of the peripheral or central nervous system, which comprises administering an effective amount of a compound of claim 1 to a host in need of such treatment or prevention.

10. A method for the treatment or prevention of an ischemic condition of the peripheral organs or limbs, comprising administering an effective amount of a compound of claim 1 to a host in need of such treatment or prevention.

11. A method of treating or preventing a state of shock, comprising administering an effective amount of a compound of claim 1 to a host in need of such treatment or prevention.

12. A method of protecting a transplant organ during surgical operation or organ transplantations, comprising administering an effective amount of a compound of claim 1 to a host in need of such treatment.

13. A method of preserving or protecting organ transplants for surgical measures, comprising bringing an effective amount of a compound of claim 1 into contact with the organ transplant.

14. A method of treating an illness in which cell proliferation is a primary or secondary cause, comprising administering an effective amount of a compound of claim 1 to a host in need of such treatment.

15. A pharmaceutical composition, comprising a compound of claim 1 and a pharmaceutically acceptable carrier.

* * * * *